April 2, 1974 A. BARBERET Plant Pat. 3,537
CARNATION PLANT (LONGANO)
Filed Nov. 10, 1972
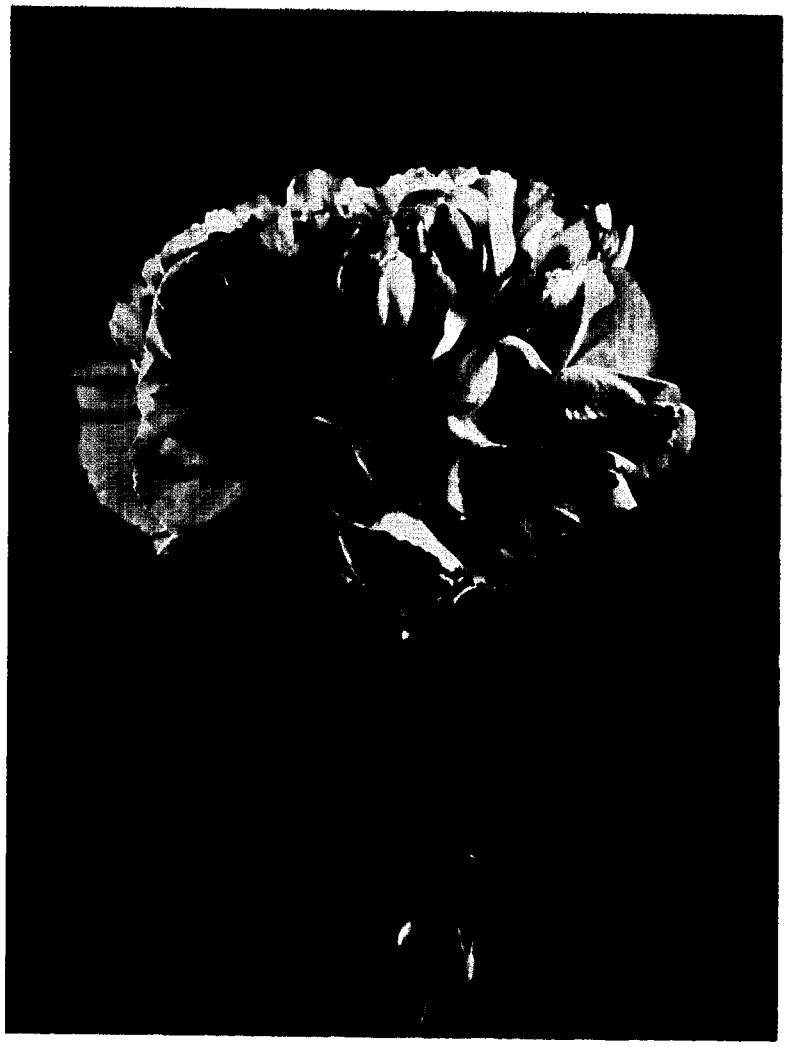

United States Patent Office

Plant Pat. 3,537
Patented Apr. 2, 1974

3,537
CARNATION PLANT

Alexandre Barberei, La Londe, France, assignor to Laboratoire de Physiologie Vegetale de la Londe Societe Civile Agricole, La Londe, France Filed Nov. 10, 1972, Ser. No. 305,348
Int. Cl. A01h 5/00
U.S. Cl. Plt.—73 1 Claim

ABSTRACT OF THE DISCLOSURE

A new variety of carnation plant originated as a sport of the unpatented variety Don Diablo (Baropat 0082F) and distinguished by its very large flower and the stability of its intense red color in wintertime.

BACKGROUND OF THE NEW PLANT

This new variety of carnation plant was discovered by me in 1970 as a sport of the unpatented variety Don Diablo (Baropat) which was then being grown for commercial purposes and under my direction at La Londe, France. The large size and bright red color of the flower, under the conditions of its growing environment, caused me to select and propagate this sport in the hope that its unusual size and color could be retained for year around culture. This sport was asexually reproduced under my direction by means of cuttings and several generations of testing have shown that this new plant has not only retained its distinctive floral characteristics but that it also has the ability to hold the intensiy of is color during wintertime culture. Asexual propagation and culture of this new plant by cuttings at La Londe, France, and under my direction has demonstrated conclusively that its distinctive features are fixed and hold true through successive generations.

DESCRIPTION OF THE DRAWING

This new variety of carnation plant is illustrated by the accompanying photographic drawing which shows the form and details of a fully developed blossom.

DESCRIPTION OF THE NEW PLANT

The following is a detailed description of my new carnation variety with the color designations according to The RHS Colour Chart published by The Royal Horticultural Society at London, England.

*The plant*

Origin: Sport.
Parent variety: Don Diablo—Baropat 0082F (Unpatented).
Classification:
*Botanic.*—Hybrid *Dianthus caryophyllus* (L.)
*Commercial.*—Perpetual flowing carnation for cut flower production.
Form: Same as the Sim types.
Height: About 50 cm. when one year old.
Growth: Vigorous and erect with normal upright branching.
Foliage: Quantity—Fairly abundant.
*Leaf shape.*—Lanceolate and up to 17.3 cm. long.
*Texture.*—Smooth.
*Color.*—Upper side—Greyed-Green 189A. Under side—Green.
*Petioles.*—None. Leaf is amplexicaul.

*The bud*

Form: Globular.
Size: Medium. Length about 30 mm. Diameter—Average 25 mm.
Opening: Bud opens slowly.

Color: Green when sepals first divide and when petals begin to unfurl.
Sepals: Upper ends curl back.
*Color.*—Inside—Pale Green. Outside—Green.
Calyx: Large, pear shaped, and rarely splits.
*Aspect.*—Smooth.

*The flower*

Blooming habit: Plant blooms continuously and profusely.
Size of bloom: Very large.
Borne: Singly.
Shape: High center, changing to dome shape as blossom matures.
Petalage: Number of Petals—66 to 80—average about 71.
*Form.*—Fan shaped with smooth margins.
*Arrangement.*—Petals tend to be imbricated.
*Color.*—Outer Petal—Red 45A to 45B with base Red Color 45C. Inside petal—Same as outer petals. Reverse side—Same coloring but less brilliant.
*Appearance.*—Satiny.
*Texture.*—Soft.
Petaloids: About 10 in number.
*Size.*—About half the size of normal petals.
*Color.*—Red.
Peduncle: Upright.
Fragrance: Just perceptible.
Persistence: Petals hang on the stem until fading.
Effect of weather: Blooms are not affected by wet or hot weather.
Lasting quality:
*On plant.*—15 days.
*As a cut flower.*—10 days.
Disease resistance: Plant resists *Fusarium roseum.*

*Reproductive organs*

Stamens:
*Anthers.*—None.
*Filaments.*—2.5 cm. long. Color—White and reddish at top.
Pistils: 2 or 3 in number, 3 cm. long when ripe.
*Stigmas.*—White with or without reddish tint.
Ovaries: Pear shaped, pale green with yellowish color at the upper part.

*Fruit*

Fertility: A little.
Shape: Pear shaped.
Color: Green and ochreous at maturity.

This new variety of carnation plant is particularly distinguished by its ability to maintain the intense red color of its very large and attractive blossoms during wintertime flowering thus retaining the same flower coloring throughout the productive life of the plant regardless of the season. Among the many red carnation varieties of the "American" type, there are very few that are able to hold the true blossom color during wintertime flowering and it is for that reason in particular that this new variety of carnation plant is believed to be important. This new plant has the further advantage of a vigorous growth habit with large leaves and strong stems and a profuse production of its flowers.

I claim:

1. The new and distinct variety of carnation plant substantially as herein shown and described, characterized by its profuse production of large flowers of intense red coloring and its ability to retain the same intense flower coloring during wintertime flowering.

No references cited.

ROBERT E. BAGWILL, Primary Examiner